US009005231B2

United States Patent
Shi

(10) Patent No.: US 9,005,231 B2
(45) Date of Patent: Apr. 14, 2015

(54) SAFE AND CONVENIENT, DISPOSABLE AUTOMATIC LANCET

(75) Inventor: Guoping Shi, Suzhou (CN)

(73) Assignee: Sterilance Medical (Suzhou) Inc., Suzhou (CN)

( * ) Notice: Subject to any disclaimer, the term of this patent is extended or adjusted under 35 U.S.C. 154(b) by 0 days.

(21) Appl. No.: 13/995,946

(22) PCT Filed: Jul. 25, 2011

(86) PCT No.: PCT/CN2011/077538
§ 371 (c)(1),
(2), (4) Date: Aug. 6, 2013

(87) PCT Pub. No.: WO2012/083690
PCT Pub. Date: Jun. 28, 2012

(65) Prior Publication Data
US 2014/0005710 A1 Jan. 2, 2014

(30) Foreign Application Priority Data
Dec. 21, 2010 (CN) .......................... 2010 1 0596791

(51) Int. Cl.
A61B 17/14 (2006.01)
A61B 17/32 (2006.01)
(Continued)

(52) U.S. Cl.
CPC ....... *A61B 17/3496* (2013.01); *A61B 5/150022* (2013.01); *A61B 5/150259* (2013.01);
(Continued)

(58) Field of Classification Search
CPC ..... A61B 5/151; A61B 17/34; A61B 17/3496
USPC .......................... 606/182, 181, 183, 167, 170; 600/573–584; 604/117, 207–211
See application file for complete search history.

(56) References Cited

U.S. PATENT DOCUMENTS

| 7,282,058 | B2 * | 10/2007 | Levin et al. | 606/181 |
| 7,322,997 | B2 * | 1/2008 | Shi | 606/181 |
| 8,740,924 | B2 * | 6/2014 | Shi | 606/182 |

FOREIGN PATENT DOCUMENTS

CN 101444428 A * 6/2009

OTHER PUBLICATIONS

Machine Translation of Chinese Patent Application 33CN101444428 (A)—no date provided.*

(Continued)

*Primary Examiner* — Katherine M Shi
*Assistant Examiner* — Mohamed Gabr
(74) *Attorney, Agent, or Firm* — Kilpatrick Townsend & Stockton LLP

(57) ABSTRACT

An improved safe and convenient disposable automatic lancet, comprising a housing (1), a needle core (2), a spring (3) and a protective rod (4), wherein, a pressing arm of a trigger button (10) is divided into a first pressing leg (11) and a second pressing leg (19), and the first pressing leg (11) is used for triggering an elastic arm in a locking structure to form a press-type trigger structure, and the second pressing leg (19) fits with a safety sleeve (20) and a press-down channel (17) to achieve a safety function of the trigger button (10); a barb (12) on the second pressing leg (19) fits with a self-locking hook (13) on the housing (1) so as to achieve a self-locking function after one press. In order to shorten the exposed needle length of a needle body on the needle core (2), in the automatic lancet, the distance between the second pressing leg (19) and the needle tip (7) is designed to be less than the distance between the first pressing leg (11) and the needle tip (7). Since the exposed needle length depends on the position of the safety sleeve (20), the exposed needle length is shortened, therefore the puncture performance increases, which enables the design of the lancet to be more reasonable and practical.

5 Claims, 9 Drawing Sheets

(51) Int. Cl.
*A61B 17/34* (2006.01)
*A61B 5/15* (2006.01)
*A61B 5/151* (2006.01)

(52) U.S. Cl.
CPC ..... *A61B5/150412* (2013.01); *A61B 5/150549* (2013.01); *A61B 5/150618* (2013.01); *A61B 5/150717* (2013.01); *A61B 5/150916* (2013.01); *A61B 5/15113* (2013.01); *A61B 5/15117* (2013.01); *A61B 5/1513* (2013.01); *A61B 5/15144* (2013.01); *A61B 5/1411* (2013.01); *A61B 5/150519* (2013.01)

(56) References Cited

OTHER PUBLICATIONS

International Publication WO 2012/083690 A1 with International Search Report.

\* cited by examiner

SAFE AND CONVENIENT, DISPOSABLE AUTOMATIC LANCET

The present application is the U.S. national phase of International Application No. PCT/CN2011/077538filed on Jul. 25, 2011, which claims the benefit of priority to Chinese Patent Application No. 201010596791.0 titled "IMPROVED SAFE AND CONVENIENT, DISPOSABLE AUTOMATIC LANCET", filed with the Chinese State Intellectual Property Office on Dec. 21, 2010, the entire disclosure of which are herein incorporated by reference.

FIELD OF THE INVENTION

The invention relates to the field of medical device, particularly relates to a disposable automatic lancet. Based on the previous safe and convenient design, the lancet has an improved puncture performance of a needle body, which makes the design of the lancet more reasonable and practical.

BACKGROUND OF THE INVENTION

Disposable automatic lancet is the main trend of today's lancet device, which has been improved and developed over years. The Chinese patent office authorized an invention patent on Apr. 7, 2010 with the title of "SAFE AND CONVENIENT DISPOSABLE AUTOMATIC LANCET", the patent number of 200810136675.3, and the authorized publication number of CN101444428B. This patent utilizes the fit of a protective rod and the internal space of an ejection chamber to allow a needle core to be set in a locked state of to-be-launched, and before use, due to the blocking effect of an end of the protective rod, the button cannot be pressed down and then the needle core is set in a safety state. When in use, the needle core can immediately enter a launching state once the protective rod is removed by screwing, and after launching, it automatically enters the locked state by locking the button through the fit of the button and housing, and cannot be used again. Compared with other disposable automatic lancets, this patent has advantages of advanced technology, easy to operate and safe to use. However, in the specific solution given in Example 2 of this patent (see its FIGS. 12 to 15), after the protective rod is removed, 11.5 mm length of the needle body of the needle core is exposed, which has a problem that the exposed length of needle is too long. Too long exposed length of needle not only increases the force of screwing the protective rod, but also results in a biggest defect that the needle is easily to bending deflected during puncture. Particularly, with the development of medical device technology, the required blood volume of the existing blood testing equipments becomes smaller and smaller, and in order to reduce algesia, the diameter of the lancet is made finer and finer, i.e. changing from the former 23 G (Φ 0.6 mm) and 26 G (Φ 0.45 mm) to the present 28 G (Φ 0.36 mm) and 30 G (Φ 0.30 mm). Such a fine lancet, if it has too long exposed length of needle, is prone to bending and deflecting during puncture, which greatly reduces the puncture performance of the needle tip. Accordingly, the object of the present invention is how to solve the problem of too-long-exposed-length of needle, and on the other hand, retain the existing safe and convenient design.

SUMMARY OF THE INVENTION

The invention provides an improved safe and convenient disposable automatic lancet, and the objective of the invention is to solve the problem of too-long-exposed-length of needle after a protective rod is removed.

In order to achieve the above-mentioned objective, the present invention provides the following technical solution: an improved safe and convenient disposable automatic lancet, comprising a housing, a needle core and a spring, wherein the needle core is provided with a needle body having a needle tip;

the housing defines an ejection chamber in which the needle core is located, wherein the needle core has one end provided with a protective rod and another end on which the spring is fixed, the protective rod has one end protruding from a needle ejecting hole and another end detachably connected to the needle core;

the housing has an elastic arm extending toward the inside of the ejection chamber for locking the needle core, a bayonet is provided on the needle core, corresponding to an end of the elastic arm, the end of the elastic arm snaps fit with the bayonet, characterized in that the housing is provided with a trigger button which has a first pressing leg and a second pressing leg, both legs are inserted into the ejection chamber, wherein in a state of to-be-launched, the distance between the second pressing leg and the needle tip is less than the distance between the first pressing leg and the needle tip; the first pressing leg is close to or contacts with the end of the elastic arm; and the second pressing leg is provided with a barb, corresponding to which a self-locking hook is provided on the housing; the self-locking hook is positioned in the press-down route of the barb when the second pressing leg, together with the barb provided thereon, is pressed downward, the barb and the self-locking hook forms a self-locking fit;

a press-down channel is left in the ejection chamber along the press-down route of the second pressing leg, the protective rod is provided with a safety sleeve, and when the protective rod is assembled, the safety sleeve covers the needle tip and occupies the space of the press-down channel to prevent the second pressing leg from pressing downward; when the protective rod is removed, the safety sleeve is withdrawn from the press-down channel to allow the second pressing leg to be pressed downward, so as to bring the barb and the self-locking hook into a self-locking fit.

The design concept and working principle of the present invention is that: based on the structure provided in the Chinese Patent CN101444428B, the present invention divides the previously designed pressing arm of the trigger button into the first and second pressing legs, wherein the first pressing leg is used for triggering the elastic arm in a locking structure to form a trigger structure of press-type, and the second pressing leg fits with the safety sleeve and the press-down channel to achieve a safety function of the trigger button, the barb on the second pressing leg fits with the self-locking hook on the housing, so as to achieve a self-locking function after one press. In order to shorten the exposed length of the needle body on the needle core, the present invention designs the distance between the second pressing leg and the needle tip to be less than the distance between the first pressing leg and the needle tip. Since the exposed length of needle depends on the position of the safety sleeve, the objective of shortening the exposed length of needle could be achieved by setting the distance between the second pressing leg and the needle tip be less than the distance between the first pressing leg and the needle tip.

With the above technical solution, the invention has the following advantages and effects compared with the prior art:

1. The exposed length of the needle body on the needle core according to the present invention is shortened, and the exposed length can be shortened for at least 4 mm compared with the prior art.

2. Since the exposed length of the needle body on the needle core is shortened, and by contrast the puncture strength of the needle tip is increased, this is advantageous to use a finer needle body. Now proved by experiments, the finest diameter of the needle body can be 33 G (0.2 mm).

3. It is possible to use finer needle body, which makes the protective rod is easier to be pulled out, and facilitate a user's use.

BRIEF DESCRIPTION THE DRAWINGS

Figure 1:
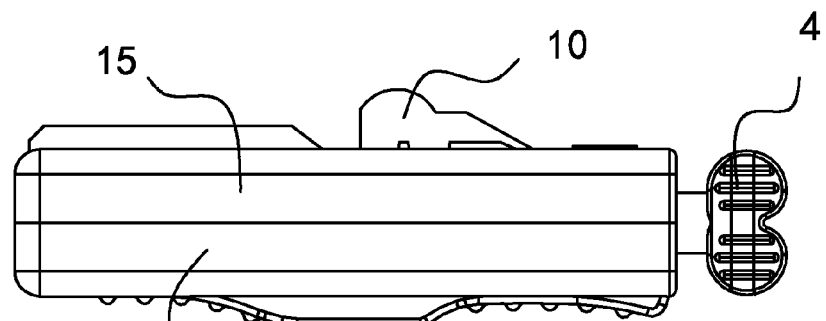
FIG. 1 shows a front view of the first embodiment of the invention.
Figure 2:
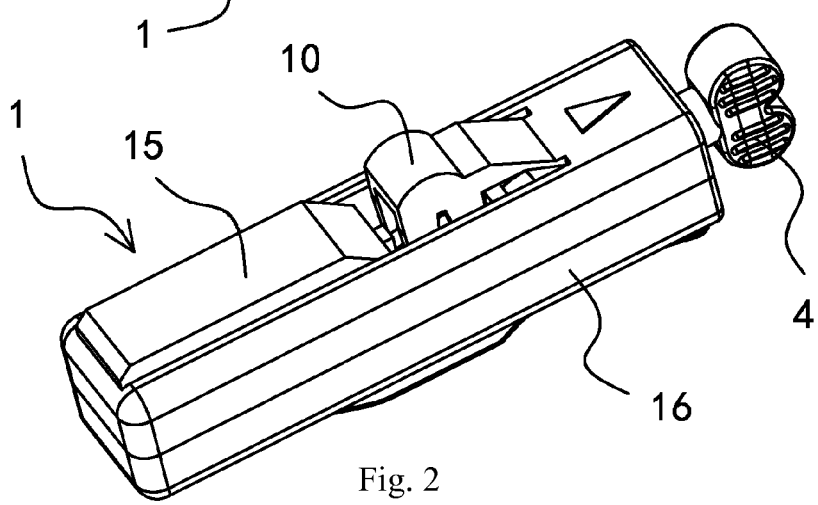
FIG. 2 shows a first perspective view of the first embodiment of the invention.
Figure 3:
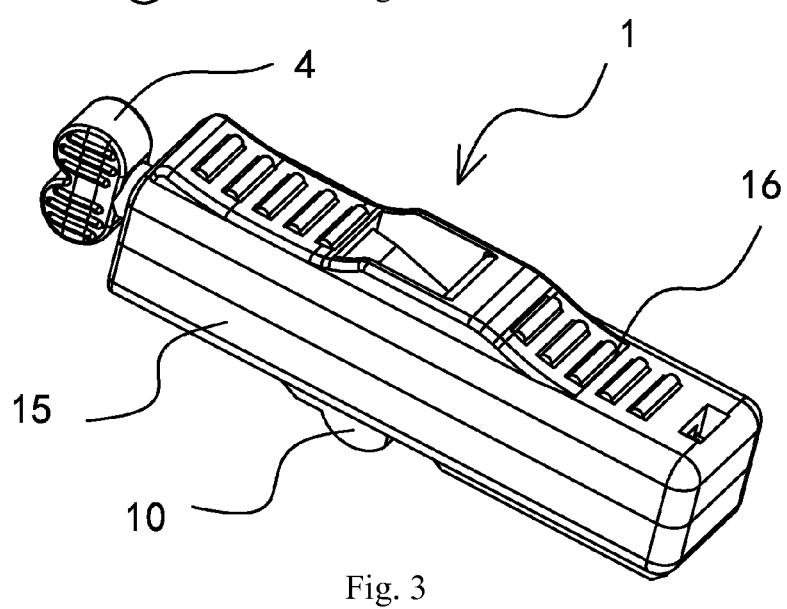
FIG. 3 shows a second perspective view of the first embodiment of the invention.
Figure 4:
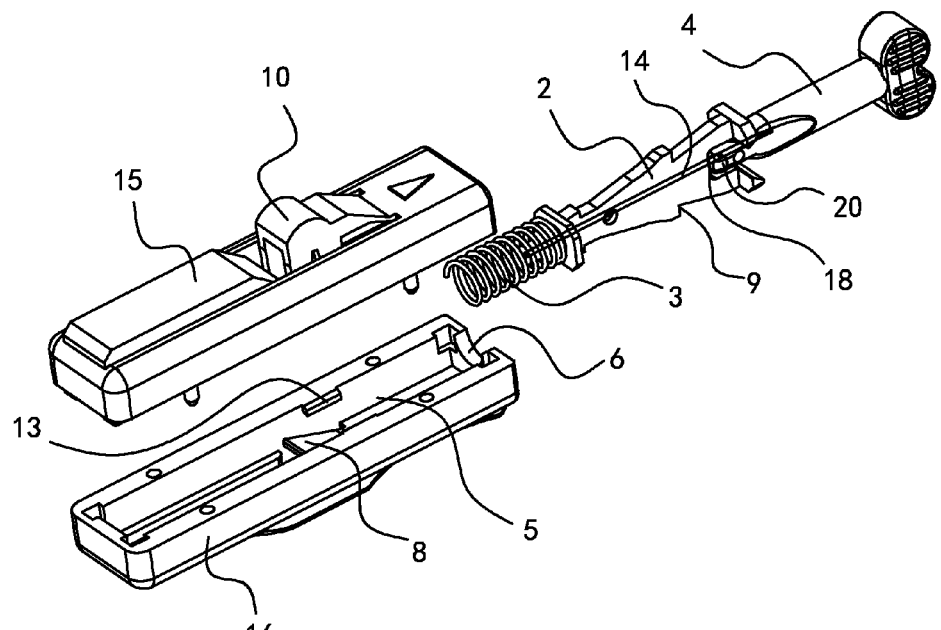
FIG. 4 shows a first exploded perspective view of the first embodiment of the invention.
Figure 5:
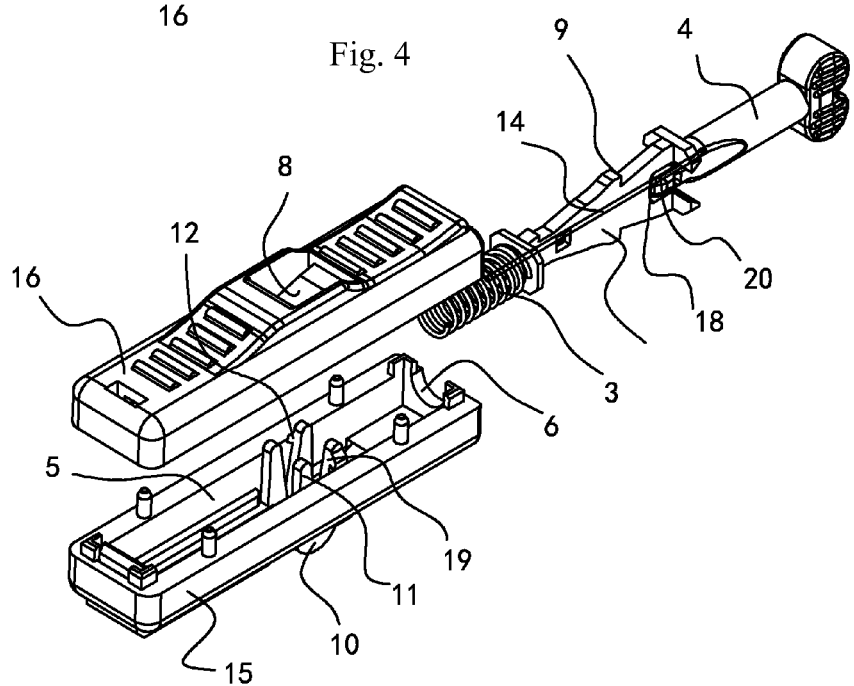
FIG. 5 shows a second exploded perspective view of the first embodiment of the invention.
Figure 6:
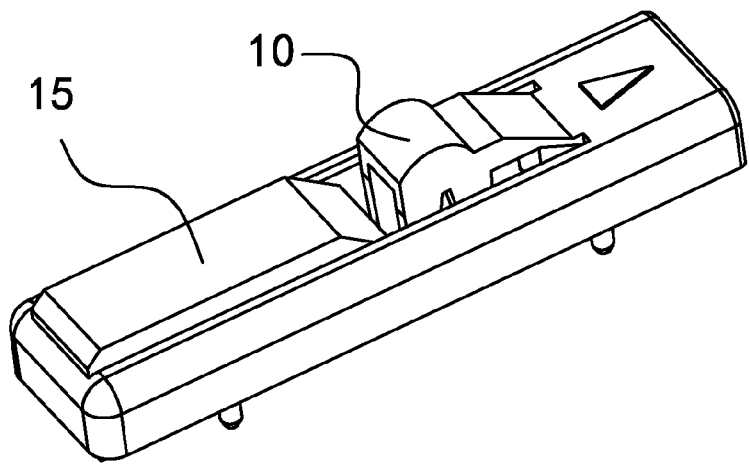
FIG. 6 shows a first perspective view of an upper cover of the housing according to the first embodiment of the invention.
Figure 7:
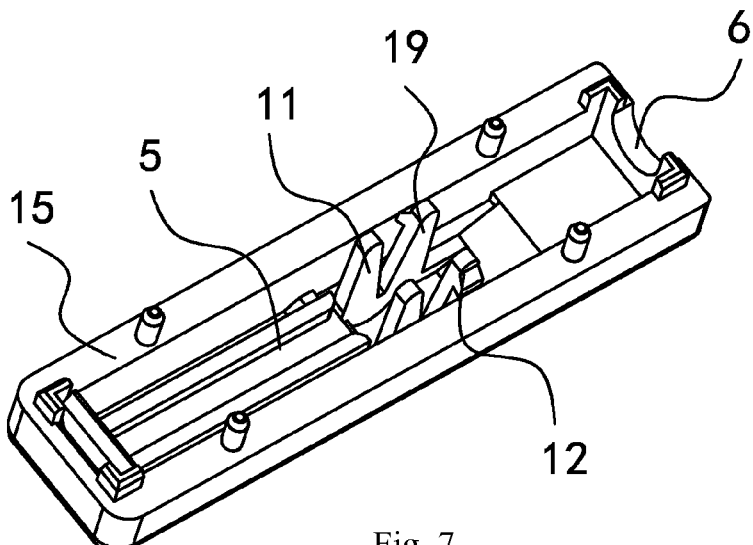
FIG. 7 shows a second perspective view of the upper cover of the housing according to the first embodiment of the invention.
Figure 8:
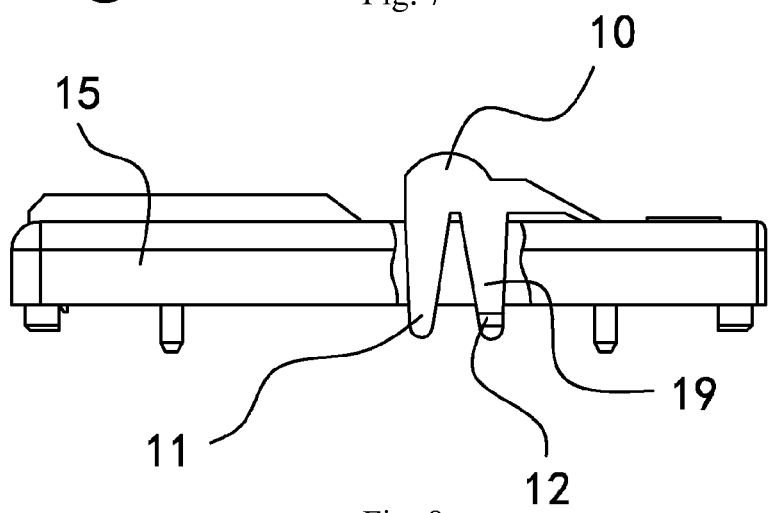
FIG. 8 shows a front view of the upper cover of the housing according to the first embodiment of the invention.
Figure 9:
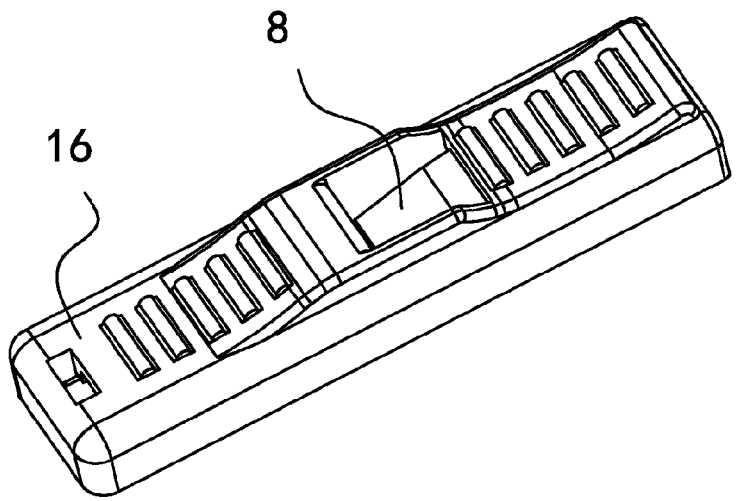
FIG. 9 shows a first perspective view of a lower cover of the housing according to the first embodiment of the invention.
Figure 10:
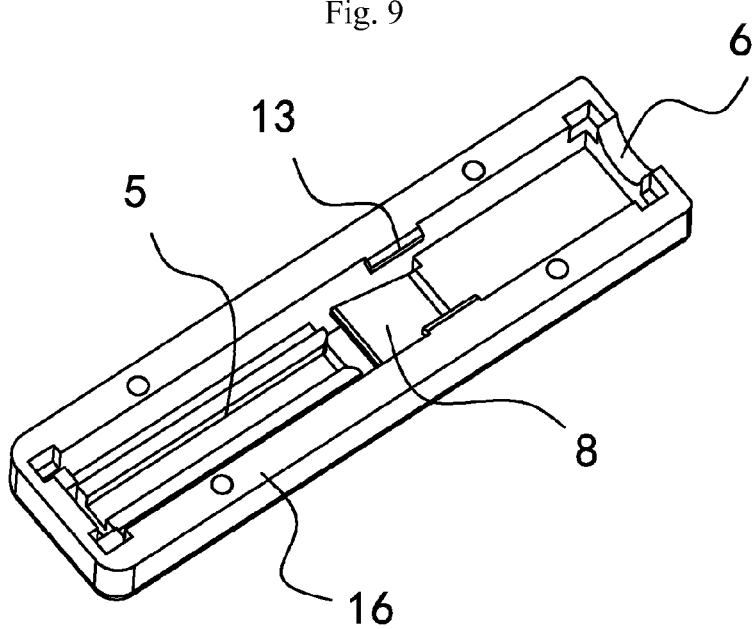
FIG. 10 shows a second perspective view of the lower cover of the housing according to the first embodiment of the invention.
Figure 11:
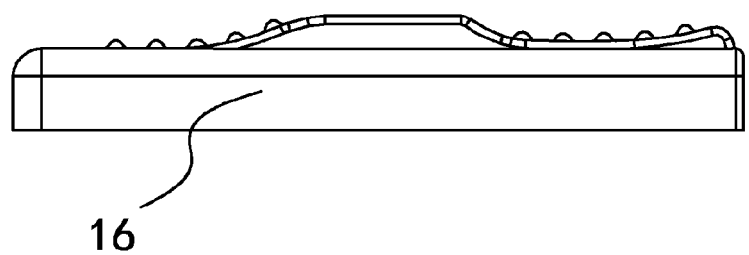
FIG. 11 show a front view of the lower cover of the housing according to the first embodiment of the invention.
Figure 12:
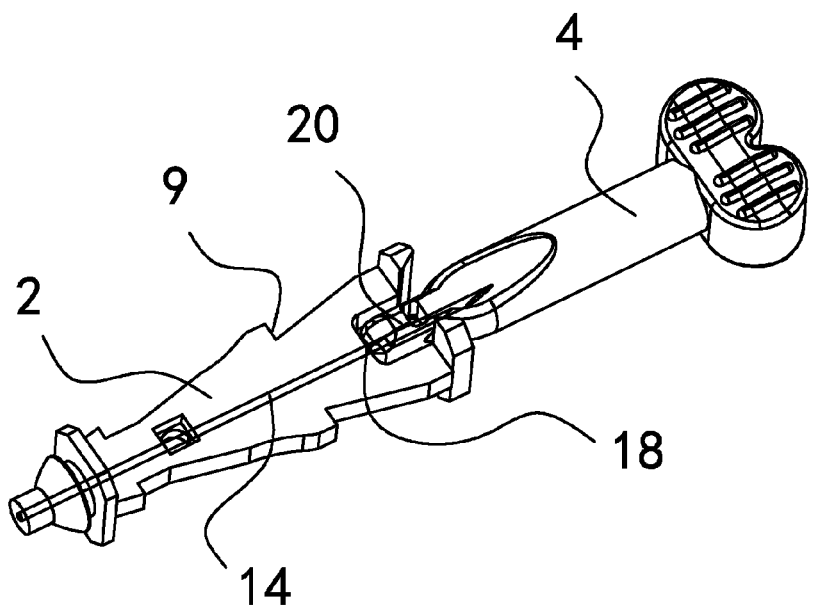
FIG. 12 shows a perspective view of the needle core and the protective rod according to the first embodiment of the invention.
Figure 13:
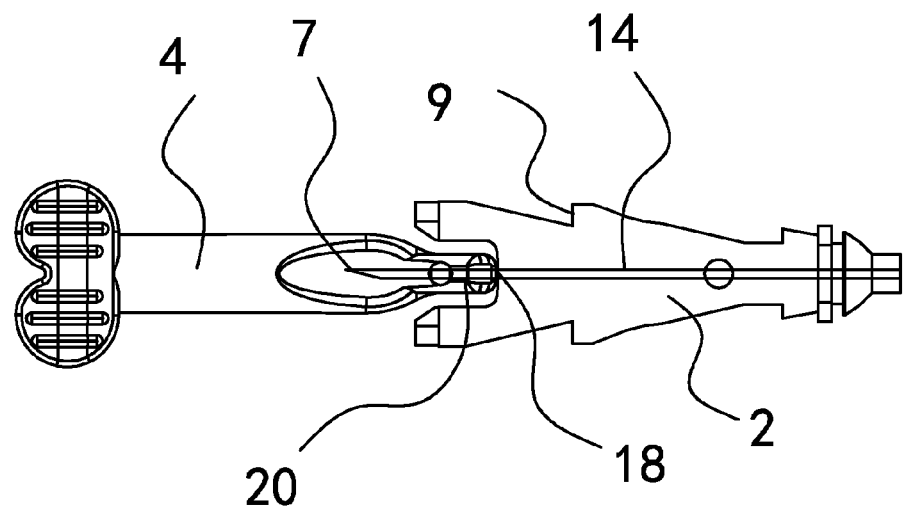
FIG. 13 shows a front view of the needle core and the protective rod according to the first embodiment of the invention.

Reference Signs in the Figures Mentioned above:
1—housing
2—needle core
3—spring
4—protective rod
5—ejection chamber
6—needle ejecting hole
7—needle tip
8—elastic arm
9—bayonet
10—trigger button
11—first pressing leg
12—barb
13—self-locking hook
14—needle body
15—upper cover
16—lower cover
17—press-down channel
18—thin neck
19—second pressing leg
20—safety sleeve
21—pressing leg

DETAILED DESCRIPTION OF THE PREFERRED EMBODIMENTS

The invention will be further described with reference to the drawings and embodiments:

Embodiment 1: An Improved Safe and Convenient Disposable Automatic Lancet

The above-mentioned technical solution is explained as follows:

As illustrated in FIGS. 1-13 and 16-18, a lancet consists of a housing 1, a needle core 2, a spring 3 and a protective rod 4. The housing 1 is composed of an upper cover 15 and a lower cover 16, which are connected into an integral structure through a hole and a pin provided in contact surfaces thereof. The housing 1 defines an ejection chamber 5 provided with a needle ejecting hole 6 in one end thereof, the needle core 2 is located in the ejection chamber 5, and one end of the needle core 2 is provided with the protective rod 4 which has one end protruding from the needle ejecting hole 6 of the housing 1, a needle body 14 is provided in the needle core 2, a needle tip 7 of the needle body 14 is positioned in the protective rod 4 and facing toward the needle ejecting hole 6, the protective rod 4 is detachably connected to the needle core 2 by virtue of a socket joint or a thin neck 18 which can be twist off, the spring 3 is arranged on the other end of the needle core 2 to form an ejection structure where the spring 3 pushes the needle core 2 to move.

An elastic arm 8 for locking the needle core 2 is extending from the bottom wall of the lower cover 16 of the housing 1 to the ejection chamber 5, and the elastic arm 8 is inclined to the ejection chamber 5. A bayonet 9 is provided on the needle core 2, corresponding to an end of the elastic arm 8, and the end of the elastic arm 8 snaps fit with the bayonet 9, to constitute a locking structure of to-be-launched after the spring 3 is compressed by the needle core 2.

The upper cover 15 of the housing 1 is provided with a trigger button 10 formed by a extended body on the housing 1 (or formed by a separate member mounted on the housing 1). The trigger button 10 is provided with a first pressing leg 11 and a second pressing leg 19, both of them are inserted into the ejection chamber 5, and in the state of to-be-launched, the distance between the second pressing leg 19 and the needle tip 7 is less than the distance between the first pressing leg 11 and the needle tip 7. The first pressing leg 11 and the second pressing leg 19 both forms a "U" shaped branch structure in the cross section perpendicular to the axis of the needle body 14, wherein, two arms of the "U" shaped branch structure of the first pressing leg 11 respectively are close to or contact with the end of the elastic arm 8 from two sides of the needle core 2 across the ejection chamber 5, to form a press-type trigger structure. Barbs 12 are respectively provided on one side, which faces toward the housing 1, of the two arms of the "U" shaped branch structure of the second pressing leg 19, one self-locking hook 13 is provided on each side of the housing 1 corresponding to each barb 12, the self-locking hook 13 is located in a press-down route of the barb 12 when the second pressing leg 19, together with the barb 12 provided thereon, is pressed downward, and the barb 12 fits with the self-locking hook 13 to form a self-locking structure after one press of the trigger button 10.

Figure 18:
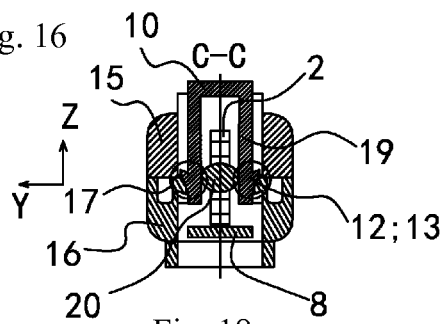
FIG. 18 shows a sectional view along a line C-C of FIG. 16.

For the second pressing leg 19, two press-down channels 17 are provided in the ejection chamber 5 to allow the "U" shaped branch structure of the second pressing leg 19 to press downward (see the circle area 17 enclosed by double-dotted line in FIG. 18). In order to clearly indicate the direction, Z direction of the press-down channel 17 is defined as the press-down direction of the second pressing leg 19, X direction is defined as the direction parallel to the axis of the needle body 14, and Y direction is defined as the direction perpendicular to the X direction and Z direction. It can be understand with reference to coordinate directions as illustrated in FIG. 18. An end of the protective rod 4, which locates in the ejection chamber 5, is provided with a safety sleeve 20, and when the protective rod 4 is assembled, the safety sleeve 20 covers the needle tip 7 and occupies part of the space of the press-down channel 17 in Y direction, to make the width of the press-down channel 17 in Y direction be less than the allowable insertion width of the second pressing leg 19, so as to prevent the second pressing leg 19 from pressing downward. When the protective rod 4 is removed, the safety sleeve 20 is withdrawn from the press-down channel 17, to make the width of the press-down channel 17 in Y direction be larger than or equal to the allowable insertion width of the second pressing leg 19, thereby allowing the second pressing leg 19 to press downward to bring the barb 12 and the self-locking hook 13 into a self-locking fit, so as to form the safety structure of the trigger button.

Figure 16:
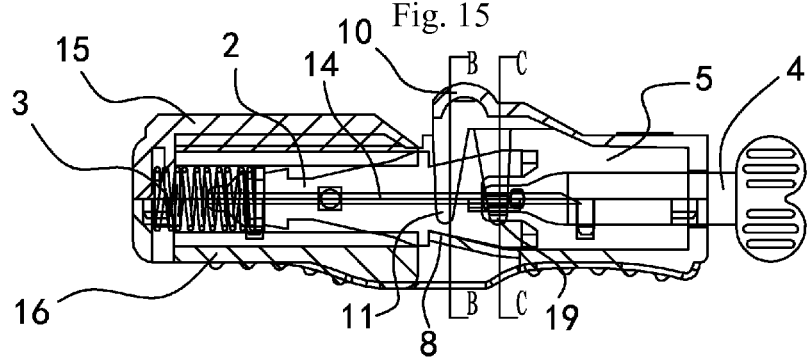
FIG. 16 shows a structure diagram of the first embodiment of the invention.
Figure 17:
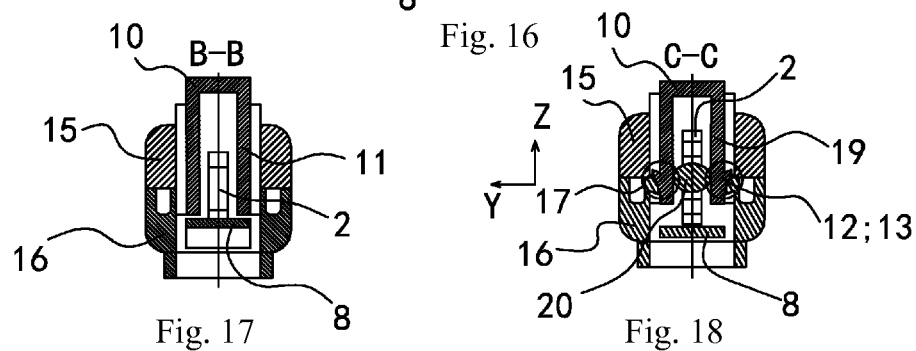
FIG. 17 shows a sectional view along a line B-B of FIG. 16.

FIGS. 6-13 separately give a configuration diagram of the upper cover 15, the lower cover 16, the needle core 2 and the protective rod 4 according to the present embodiment, and FIGS. 16-18 give assembly drawings of the embodiment. From the figures, details in all parts and the connection relationship under assembly state of the housing 1, the needle core 2 and the protective rod 4 can be clearly seen.

The invention allows the needle core to be assembled into the locking state of to-be-launched during manufacture of the lancet (it also may be not assembled into the locking state of to-be-launched, but one action of pushing the protective rod 4 should be added in use). As shown in FIGS. 16-18, in such state, due to the protective rod 4 is not removed, the trigger button 10 is under protective status, phenomenon of erroneous emission will not occur. When in use, as long as the protective rod 4 is twist off by the health care workers, the lancet will be entered into the state of to-be-launched (after the protective rod 4 is twist off, the protective rod 4 and the needle core 2 is cracked on the thin neck 18, and after the protective rod 4 is removed, the safety sleeve 20 is withdrawn from the press-down channel 17). At this time when the trigger button 10 is pressed, the second pressing leg 19 is allowed to be pressed downward, and the first pressing leg 11 is pressed the elastic arm 8 to make the needle core 2 and the housing 1 unhooked, thereby the needle core 2 is pushed by the spring 3 to inject. At the same time, the second pressing leg 19 is beyond the self-locking hook 13 during press-down movement. Accordingly during rebound process, the barb 12 is locked in a position of the self-locking hook 13 and form self-locking, which cannot return to its original state, so that locking-ejection structure is failed and it cannot be used again.

In the present embodiment, the elastic arm 8 is designed to lock the needle core 2, and it can be designed into many forms which fall into the protection scope of the invention as long as the objective of locking and unlocking the needle core 2 is achieved by utilizing the elasticity of the elastic arm 8 to fit with the bayonet 9 of the needle core 2. Wherein, the elastic arm 8 is best to be set inclined, and the inclined direction can be shown in FIG. 18, and the elastic arm 8 can also be set in the opposite direction, and then a hook is used to hook the bayonet 9.

Figure 14:
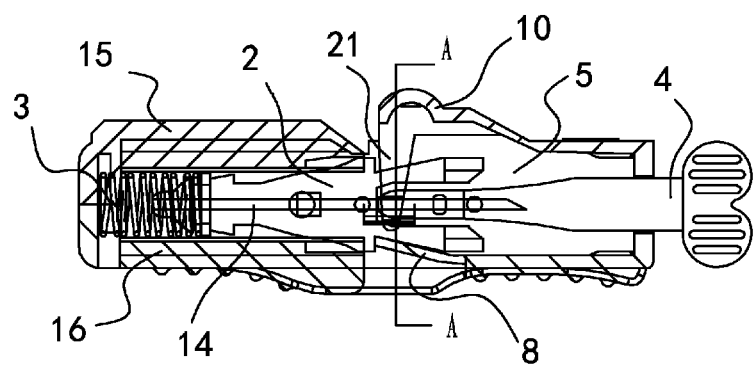
FIG. 14 shows a structure diagram of closest prior art.
Figure 15:
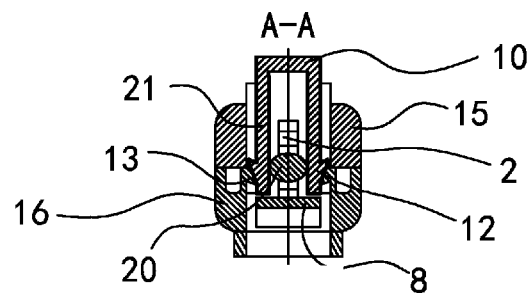
FIG. 15 shows a sectional view along a line A-A of FIG. 14.

FIGS. 14 and 15 are the schematic structure of the closest prior art (Example 2 of Chinese Patent CN101444428B). As can be seen from FIGS. 14 and 15, the prior art is characterized in that: a pressing leg 21 with only one pair of "U" shaped branch structure is provided on the trigger button 10 of the upper cover 15. When the trigger button 10 is pressed after the protective rod 4 is removed, the pressing leg 21 pushes the elastic arm 8 on the lower cover 16, and after the needle core 2 is separated and injected from the elastic arm 8, the pressing leg 21 makes the bard 12 and the self-locking hook 13 on the lower cover 16 be locked with each other during the press-down process, and the product can no longer be used after injection. However, after the protective rod 4 on the needle core 2 is twist off, front portion of the needle body 14 on the needle core 2 is exposed too long, which is prone to bending deformation during puncturing skin, reducing the puncture performance of the needle body.

FIGS. 16-18 shows assembly diagram of the present embodiment of the invention, as can be seen from the figures, the invention is characterized in that: spaced apart pressing legs with two pairs of "U" shaped branch structure i.e. the first pressing leg 11 and the second pressing leg 19 are spaced apart (see FIG. 5), are provided on the front and rear of the trigger button 10 of the upper cover 15, and in the state of to-be-launched as shown in FIG. 16, the distance between the second pressing leg 19 and the needle tip 7 is less than that between the first pressing leg 11 and the needle tip 7. When the trigger button 10 is pressed after the protective rod 4 is removed, the first pressing leg 11 on the left pushes arm 8 on the lower cover 16, and after the needle core 2 is separated and ejected from the elastic arm 8, during the press-down process the second pressing leg 19 makes the bard 12 and the self-locking hook 13 on the lower cover 16 be locked with each other, and the product can no longer be used after ejection. The key of the invention is that the pressing leg is divided into two pairs from the original one pair, with maintaining the formal functions (that is, firstly the connection between the safety sleeve 20 and the press-down channel 17 provides safety before use, secondly the fit between the bard 12 on the second pressing leg 19 and the self-locking hook 13 on the lower cover 16 provides safety after use, and thirdly the needle core 2 is assembled to be entered into the locking state of to-be-launched to provide convenience of use), and the effect of shortening the exposed length of needle is achieved.

Figure 19A:
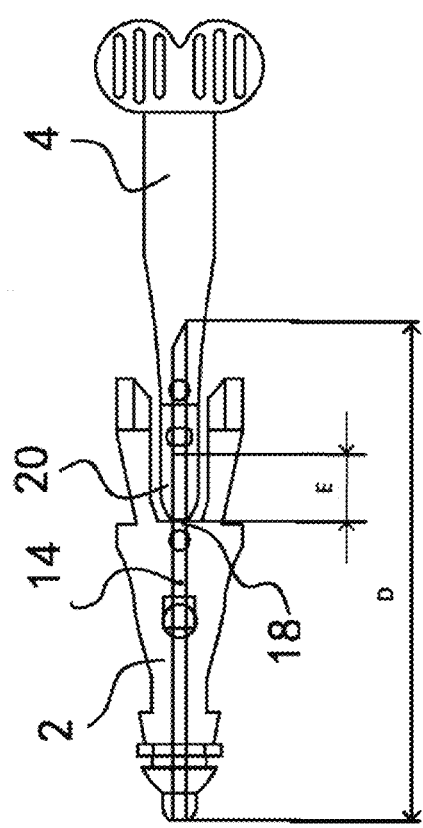
FIG. 19a shows a prior art comparison view of the exposed needle length before use.
Figure 19B:
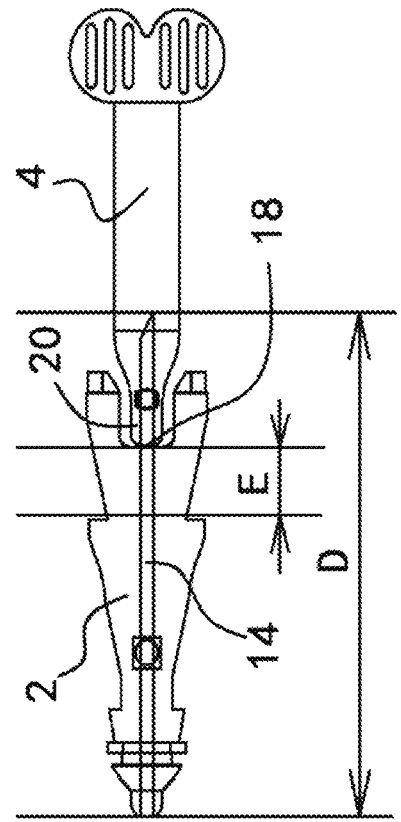
FIG. 19b shows a comparison view of the exposed needle length before use.
Figure 20A:
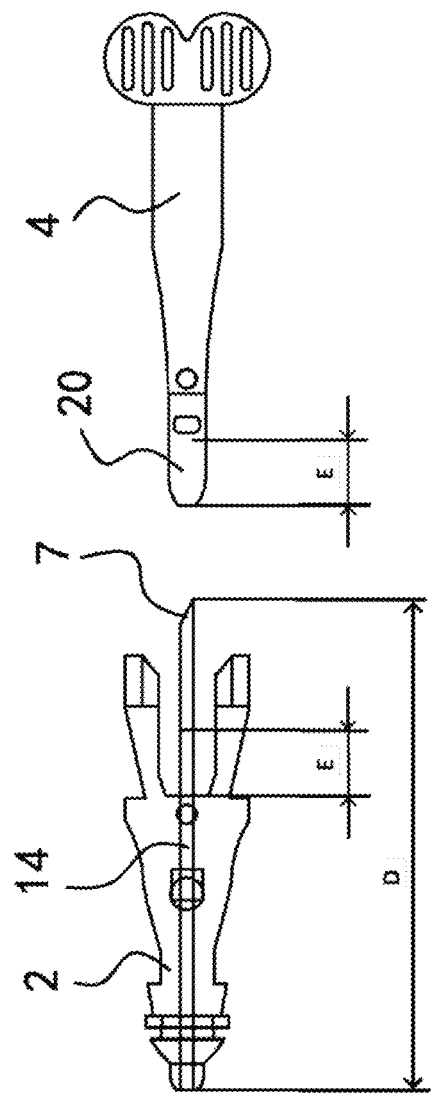
FIG. 20a shows a prior art comparison view of the exposed needle length after use.
Figure 20B:
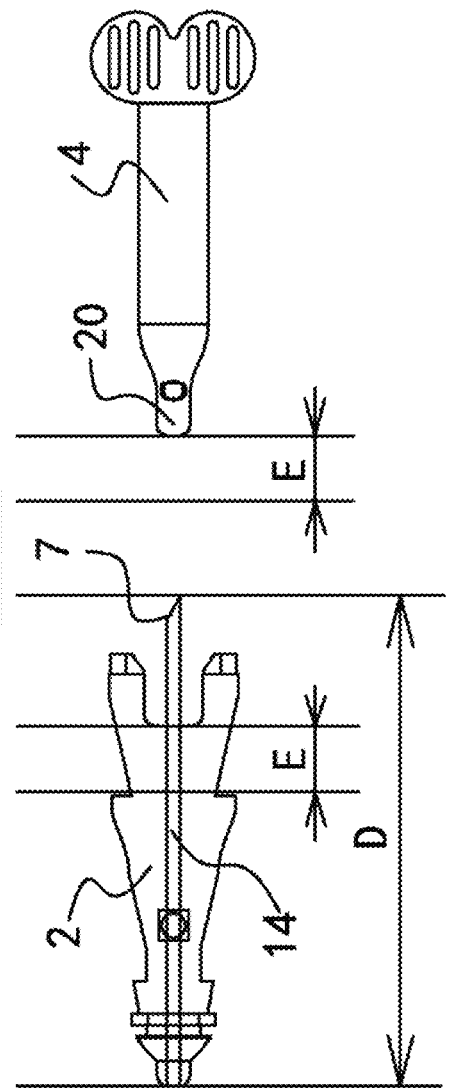
FIG. 20b shows a comparison view of the exposed needle length after use.

FIGS. 19*a* and 19*b* and 20*a* and 20*b* respectively show a comparison diagram of the exposed needle length before use and after use, wherein the word "D" indicates the length of the needle body 14, and the word "E" indicates a shorten value of the exposed needle length. FIG. 19*a* shows the state of the needle core 2 and the protective rod 4 of the prior art before use, and FIG. 19*b* show the state of needle core 2 and the protective rod 4 of the invention before use. FIG. 20*a* shows the state of the needle core 2 and the protective rod 4 of the prior art after use, and FIG. 20b shows the state of the needle core 2 and the protective 4 of the invention after use. Comparing the two figures, it can be seen clearly that the exposed needle of the prior art is longer than that of the invention, and the difference therebetween is E.

Embodiment 2: An Improved Safe and Convenient Disposable Automatic Lancet

Figure 21:
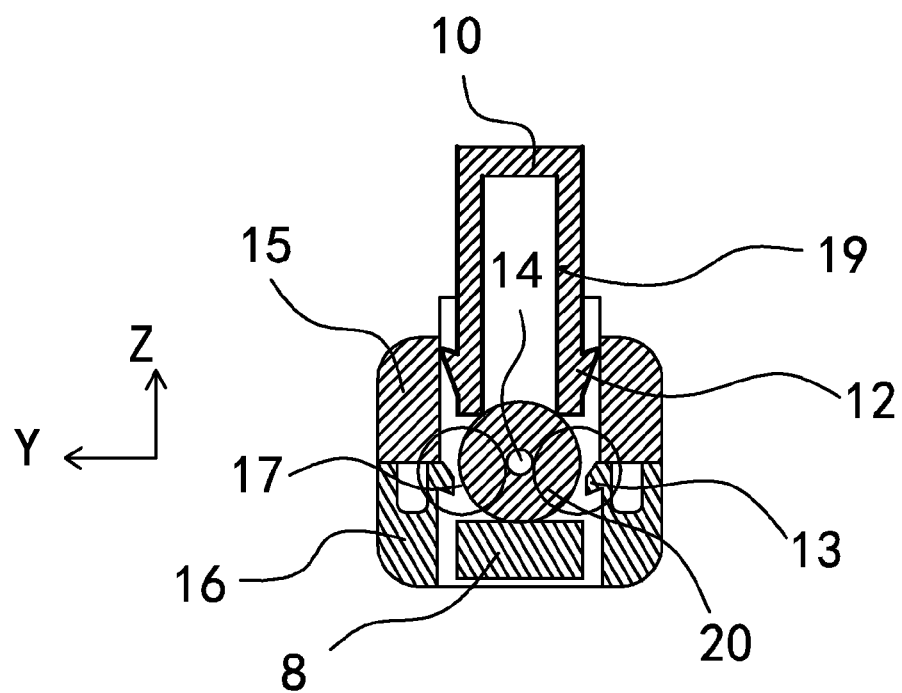
FIG. 21 shows a sectional view of safety structure of the trigger button according to the second embodiment of the invention.

As shown in FIG. 21, the difference between this embodiment and the first embodiment is that: the safety sleeve 20 covers the front part of the needle body 14, the safety sleeve 20 occupies the two press-down channels 17 (with reference to the circle area enclosed by double-dotted line, indicated by reference number 17 in FIG. 21) in Z direction (as illustrated in the coordinate of FIG. 21), to block the press-down channels 17 in Z direction, thereby preventing the second pressing leg 19 from pressing downward. When the protective rod 4 is removed, the safety sleeve 20 is withdrawn from the two pressing channels 17, to make the two pressing channels 17 be opened in direction Z, thereby allowing the barb 12 and the self-locking hook 13 to be self-locking fit when the second pressing leg 19 pressing downward, so as to form the safety structure of the trigger button. Other structure and principles are the same as that of the first embodiment, and which is not repeated here.

As can be seen from the above two embodiments that, "the safety sleeve 20 simultaneously occupies the press-down channels 17 from the Y direction and Z direction" means that, the width of the Y direction is less than the allowable insertion width of the second pressing pin 19, while Z direction is clogged. This is easy to be understood by the person skilled in the art.

The above described embodiment are to illustrate the technical concept and character of the invention, the purpose of which is to make the person skilled in the art to be able to understand the content of the invention and to carry out the invention, without limiting the protection scope of the invention. The equivalent changes or modifications according to the script of the invention should be fallen into the protection scope the invention.

What is claimed is:

1. An improved safe and convenient disposable automatic lancet, comprising a housing (1), a needle core (2) and a spring (3), wherein:
    the needle core (2) is provided with a needle body (14) having a needle tip (7);
    the housing (1) defines an ejection chamber (5) in which the needle core (2) is located, wherein the needle core (2) has one end provided with a protective rod (4) and another end fixed with the spring (3), the protective rod (4) has one end protruding from a needle ejecting hole (6) and another end detachably connected to the needle core (2);
    the housing has an elastic arm (8) extending toward the inside of the ejection chamber(5), for locking the needle core (2), a bayonet (9) is provided on the needle core (2), corresponding to an end of the elastic arm (8), and the end of the elastic arm (8) snaps fit with the bayonet (9), wherein the housing (1)is provided with a trigger button (10) which has two spaced apart sets of pressing legs, wherein each set of the pressing leg comprising a first pressing leg (11) and a second pressing leg (19), wherein the first and second pressing leg are spaced apart, both set of the pressing legs are inserted into the ejection chamber(5), wherein in a state of to-be-launched, a first distance between each of the second pressing leg (19) and the needle tip (7) is less than a second distance between each of the first pressing leg (11) and the needle tip (7); each of the first pressing leg (11) is close to or contacts with the end of the elastic arm (8); and each of the second pressing leg (19) is provided with a barb (12), corresponding to which a self-locking hook (13) is provided on the housing (1); the self-locking hook (13) is positioned in a press-down route of the barb (12) when each of the second pressing leg (19), together with the barb (12) provided thereon, is pressed downward, the barb (12) and the self-locking hook (13) forms a self-locking fit;
    a press-down channel (17) is left in the ejection chamber (5), along the press-down route of the second pressing leg (19); the protective rod (4) is provided with a safety sleeve (20), and when the protective rod (4) is assembled, the safety sleeve (20) covers the needle tip (7) and occupies the space of the press-down channel (17) to prevent the second pressing leg (19) from pressing downward; when the protective rod (4) is removed, the safety sleeve (20) is withdrawn from the press-down channel (17) to allow the second pressing leg (19) to be pressed downward, so as to bring the barb (12) and the self-locking hook (13) into a self-locking fit.

2. The lancet of claim 1, wherein when the protective sleeve (20) occupies the press-down channel (17), a width of the press-down channel (17) is less than an allowable insertion width of the second pressing leg (19), and when the protective sleeve (20) is removed from the press-down channel (17), the width of the press-down channel (17) is equal to or larger than the allowable insertion width of the second pressing leg (19).

3. The lancet of claim 1, wherein when the protective sleeve (20) occupies the press-down channel (17), the press-down channel (17) is blocked, and when the protective sleeve (20) is removed from the press-down channel (17), the press-down channel (17) is opened.

4. The lancet of claim 1, wherein the first pressing leg (11) and the second pressing leg (19) are both "U" shaped branch structure in the cross section perpendicular to the axis of the needle body (14), wherein, the "U" shaped branch structure of the first pressing leg (11) and the second pressing leg (19) respectively are close to or contact with the end of the elastic arm (8) from two sides of the needle core (2) and across the ejection chamber (5), each of the two arms of the "U" shaped branch structure of the second pressing leg (19) is provided with the barb (12) on one side of the arm facing toward the housing (1), and on each side of the housing (1) corresponding to the barb (12), one self-locking hook (13) is provided.

5. The lancet of claim 1, wherein the elastic arm (8) is inclined to the ejection chamber (5).

* * * * *